United States Patent
Hong et al.

(10) Patent No.: US 12,263,259 B1
(45) Date of Patent: Apr. 1, 2025

(54) SPLIT TYPE STERILIZATION ELECTROLYTIC SILVER ION SPRAY DEVICE

(71) Applicant: Huiping Hong, Guangdong (CN)

(72) Inventors: Huiping Hong, Guangdong (CN); Weiqi Xu, Guangdong (CN)

(*) Notice: Subject to any disclaimer, the term of this patent is extended or adjusted under 35 U.S.C. 154(b) by 0 days.

(21) Appl. No.: 18/765,061

(22) Filed: Jul. 5, 2024

(30) Foreign Application Priority Data

May 30, 2024 (CN) .................. 202421211519.X

(51) Int. Cl.
| | | |
|---|---|---|
| A61L 9/00 | (2006.01) | |
| A61L 2/03 | (2006.01) | |
| A61L 2/18 | (2006.01) | |
| A61L 2/22 | (2006.01) | |
| A61L 2/26 | (2006.01) | |
| A61L 9/14 | (2006.01) | |
| A61L 9/16 | (2006.01) | |
| C25B 15/00 | (2006.01) | |
| C25C 1/20 | (2006.01) | |
| C25C 7/02 | (2006.01) | |
| A61L 101/02 | (2006.01) | |

(52) U.S. Cl.
CPC .............. *A61L 2/035* (2013.01); *A61L 2/18* (2013.01); *A61L 2/22* (2013.01); *A61L 2/26* (2013.01); *A61L 9/145* (2013.01); *A61L 9/16* (2013.01); *C25C 1/20* (2013.01); *C25C 7/02* (2013.01); *A61L 2101/02* (2020.08); *A61L 2202/11* (2013.01); *A61L 2202/15* (2013.01); *A61L 2202/16* (2013.01); *A61L 2209/134* (2013.01); *A61L 2209/213* (2013.01)

(58) Field of Classification Search
CPC .............. C02F 1/461; B01J 19/08; C25B 1/00
USPC .......... 422/292, 306; 205/701, 705; 204/232
See application file for complete search history.

(56) References Cited

U.S. PATENT DOCUMENTS

| | | | |
|---|---|---|---|
| 2008/0067078 A1* | 3/2008 | Kitaori | A61L 2/0088 |
| | | | 204/252 |
| 2020/0128883 A1* | 4/2020 | Yamada | A24F 40/53 |

* cited by examiner

*Primary Examiner* — Monzer R Chorbaji
(74) *Attorney, Agent, or Firm* — Hemisphere Law, PLLC; Zhigang Ma

(57) ABSTRACT

The present invention relates to split type sterilization electrolytic silver ion spray device in the field of cosmetics technology, which comprises sprinkler head, bottle body and electrolytic device comprising anode, decorative cover, cathode, electrolytic device shell, circuit board, lithium battery and electrolytic device base. The electrolytic device is equipped with resin tank, effectively capturing and adsorbing free silver ions, and greatly preventing them released by the anode during the electrolysis process from being reduced to silver metal by stacking at the cathode. The adsorbed silver ions can be soaked in hot water to increase the porosity of the resin, so that they are released, and help increase the content of silver ions in the preparation solution. This device is suitable for various occasions and uses, whether it is home, office, hospital or public places, this device can be used for air disinfection and sterilization. Moreover, it can be used for surface disinfection treatment to meet the disinfection requirements of different places and needs.

20 Claims, 4 Drawing Sheets

SPLIT TYPE STERILIZATION ELECTROLYTIC SILVER ION SPRAY DEVICE

TECHNICAL FIELD

The present invention relates to the field of cosmetics technology and specifically is split type sterilization electrolytic silver ion spray device.

BACKGROUND OF THE PRESENT INVENTION

Electrolytic silver ion antivirus technology is a technology that utilizes the antibacterial properties of silver ions to achieve disinfection and sterilization. Silver ion (Ag+) is one of the most active of metal ions, and its antibacterial effect is long-lasting and particularly strong. In the presence of light and water, silver ions will be activated, producing reactive oxygen species (OH−). This reactive oxygen species has several times the oxidative decomposition capacity of ultraviolet ray and ozone, and has a killing and decomposition effect on bacteria and viruses. Electrolysis is a commonly used method to obtain silver ions. In the process of electrolysis, the anode (positive electrode) and cathode (negative electrode) are placed in the electrolyte solution. When the current passes through, the silver atom on the anode lose electrons to become silver ions (Ag+) and are released into the solution. At the same time, silver will precipitate out of the cathode. This is a REDOX process, in which the anode undergoes an oxidation reaction and silver atoms are oxidized into silver ions, while the cathode undergoes a reduction reaction. Silver ions in the solution receive electrons, which are reduced into silver atoms and deposited on the cathode. In this process, part of the silver ions will be released into the electrolyte solution, so that the electrolyte solution has the ability to antibacterial and sterilization.

After the bottled disinfectant of electrolytic silver ion spray device is used up, the bottle usually becomes waste, increasing the pressure of garbage disposal and causing a certain burden on the environment. The massive use of disposable products not only generates a large amount of plastic waste, but also may consume a large amount of resources and emit pollutants during the process of manufacturing and transportation. For consumers, each time they run out of disinfectant, they need to buy new bottled products, which undoubtedly increases the cost of use. In the long run, this cost accumulation may cause a certain pressure on the economy of individuals or families. Bottled disinfectant is usually large and not easy to carry, which may bring inconvenience to people who need to go out or travel frequently. At the same time, for users with limited family or office space, storage is also a problem.

SUMMARY OF PRESENT INVENTION

In view of the shortcomings of the existing technology, the present invention provides split type sterilization electrolytic silver ion spray device, which has the advantages that the device can be used circularly, the portable design is convenient for users to use at any time and any place, and the present invention is suitable for a plurality of occasions and purposes, solving the problems raised in the background technology.

The present invention provides the following technical schemes: split type sterilization electrolytic silver ion spray device comprises a sprinkler head, a bottle body and an electrolytic device. The electrolytic device comprises an anode, a decorative cover, a cathode, an electrolytic device shell, a circuit board, a lithium battery and an electrolytic device base. The bottom of the electrolytic device shell is clamped with an electrolytic device base, the top of the electrolytic device base is equipped with a lithium battery, the lithium battery is electrically connected with a circuit board, the circuit board is electrically connected with a cathode and an anode, and the top of the cathode is equipped with a decorative cover, and the interior of the cathode is equipped with an anode.

Preferably, the electrolytic device shell is equipped with a screw groove inside, and the internal thread of the screw groove is connected with a bottle body, the surface of the bottle body is fitted with the seal ring, and the outer arc of the seal ring is fitted with the electrolytic device shell.

Preferably, the electrolytic device is internally provided with a resin tank, the resin tank comprises a resin tank cover and a resin tank body, the surface of the anode is provided with a resin tank body, and the top of the resin tank body is equipped with a resin tank cover.

Preferably, the bottom of the electrolytic device is equipped with a non-slip mat, and the top of the bottle body is equipped with a sprinkler head.

Preferably, the left side of the outer arc of the bottle body is equipped with a charging port, and the right side of the outer arc of the bottle body is equipped with an electrolytic switch.

Compared with existing technologies, the present invention has the following beneficial effects:

The split type germicidal electrolytic silver ion spray device. In this scheme, tap water is put into the bottle in advance, and then silver ions are obtained through the electrolytic device. The preparation solution is stored in the bottle, and then the prepared silver ion solution is applied to the items that need to be purified by the sprinkler head. Because the anode material in the electrolytic device is a silver metal simple substance, and the lithium battery is controlled by the electrolytic switch to achieve discharge, forming a circuit. At this time, the anode surface immersed in the water undergoes an oxidation reaction, the silver atoms lose electrons and become silver ions and release into the solution. In this process, when there are enough silver ions in the water, they will obtain electrons on the cathode and restore to silver atoms and deposit on the cathode. In order to prevent the silver ions in the water body from been reduced to the maximum extent, we have added a resin tank inside. The resin tank is equipped with silver ion exchange resin which can effectively capture and adsorb free silver ions. The circuit board can automatically control the electrolysis time. After the electrolysis is completed, the power is automatically cut off. Part of the adsorbed silver ions during electrolysis can be washed with hot water to increase the porosity of resin, so as to release silver ions, assisting in increasing the silver ion content in the preparation solution, and generate silver ions that have a strong bactericidal effect through electrolysis. Silver ions can destroy the cell wall of bacteria, so that the bacteria can be inactivated, so as to achieve the effect of efficient disinfection. This sterilization method is fast and effective, which can quickly kill bacteria in the air and reduce the spread of pathogens. Compared with traditional chemical disinfectants, the silver ions used in electrolytic silver ion spray devices are safer and environmentally-friendly, and silver ions are harmless to human beings. Do not produce irritating odor or harmful substances. It is harmless to the environment and human health.

At the same time, the silver ion spraying device does not produce secondary pollution during use. It is environmentally-friendly and can be recycled. The electrolytic silver ion spray device is simple and convenient to operate, and users can only operate according to the instructions. In addition, it has a portable design, which is convenient for users to use at any time and anywhere. Only tap water needs to be added, and liquid for disinfection and sterilization can be produced after electrolysis. The electrolytic device is equipped with a resin tank, which can effectively capture and adsorb free silver ions, and to a large extent prevent the silver ions released by the anode during the electrolysis process from being reduced to silver metal by stacking at the cathode. The adsorbed silver ions can be soaked in hot water to increase the porosity of the resin, so that silver ions are released, assisting in increasing the content of silver ions in the preparation solution. The electrolytic silver ion spray device is suitable for a variety of occasions and uses, whether it is home, office, hospital or public places, this device can be used for air disinfection and sterilization. In addition, it can also be used for the disinfection treatment of object surfaces to meet the disinfection requirements of different places and needs.

In the figures: 1. Sprinkler head; 2. bottle body; 3. electrolytic device; 4. resin tank; 5. resin tank cover; 6. resin tank; 7. anode; 8. Decorate the cover plate; 9. Cathode; 10. electrolytic device shell; 11. circuit board; 12. lithium battery; 13. electrolytic device base; 14. non-slip mat; 15. electrolytic switch; 16. charging port; 17. seal ring.

DETAILED DESCRIPTION OF THE EMBODIMENT'S

The following will provide a clear and complete description of the technical solution in the embodiments of the present invention, in conjunction with the drawings attached to the embodiments of the present invention. Obviously, the embodiments described are only a part of the embodiments of the present invention, but not all of them. Based on the embodiments of the present invention, all other embodiments obtained by ordinary technical personnel in the field without making creative labor belongs to the scope of protection of the present invention.

Figure 1:
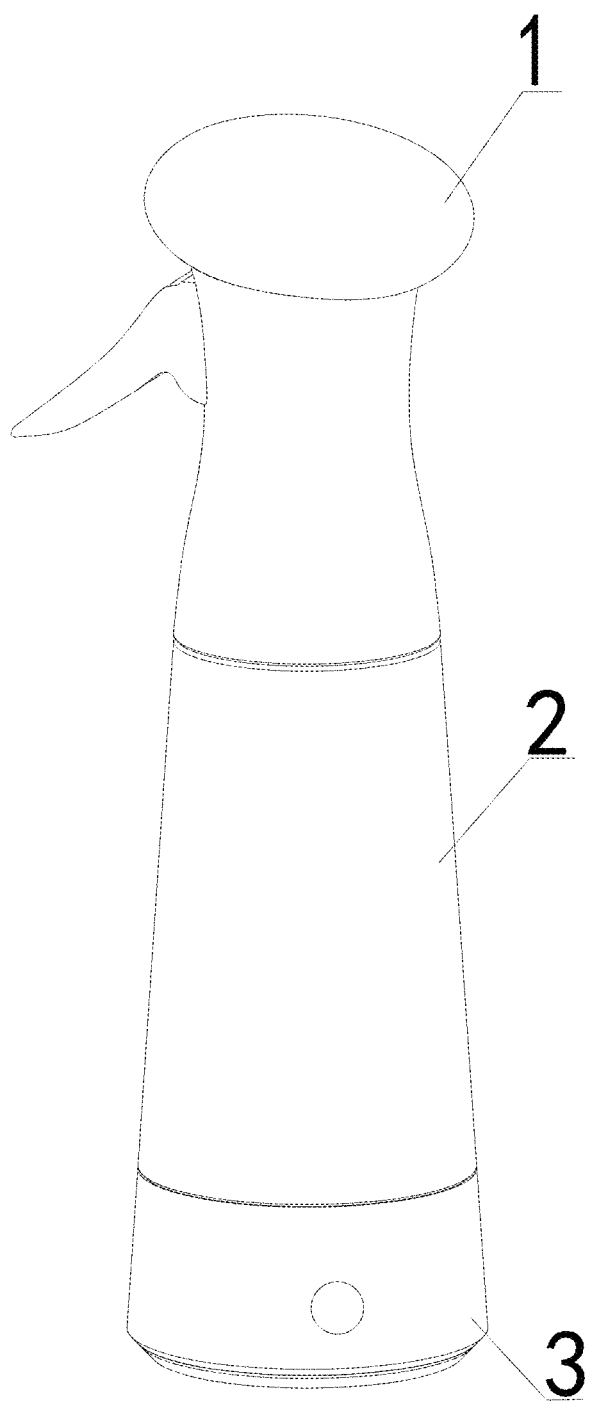
FIG. 1 is a schematic diagram of the overall structure of the device of the present invention.
Figure 2:
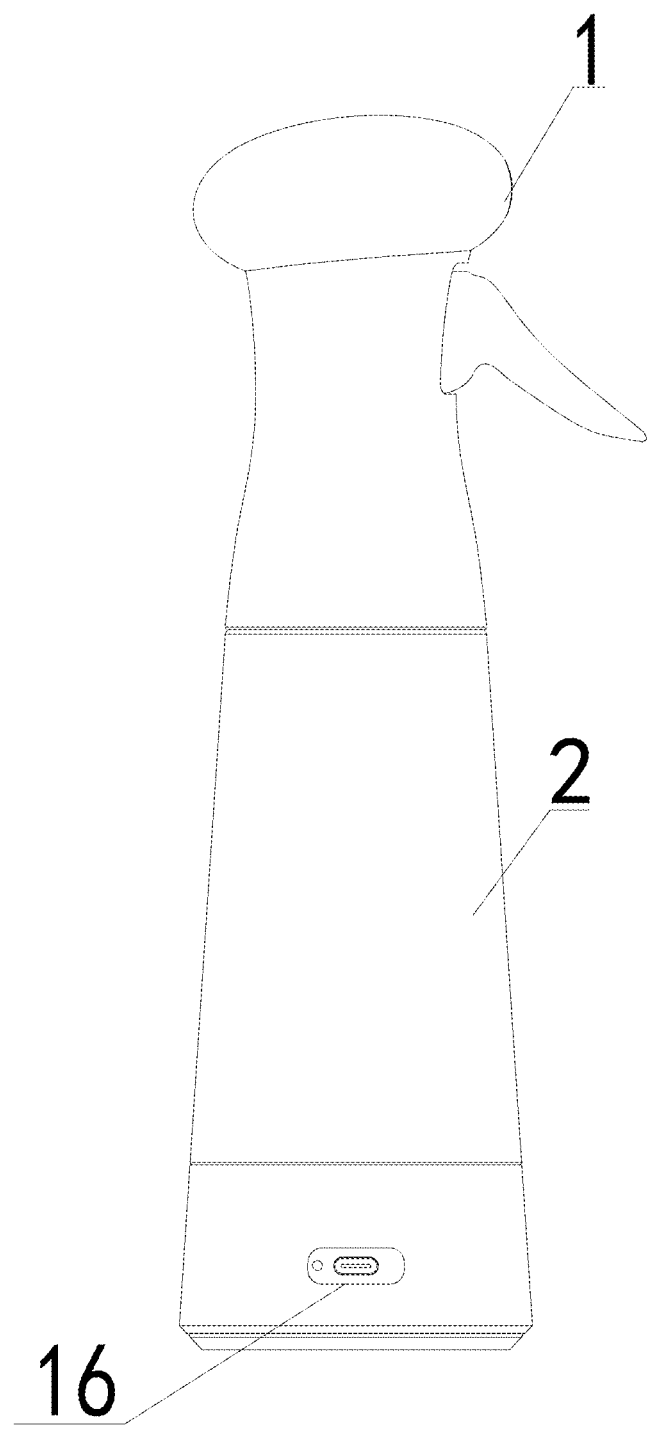
FIG. 2 is a schematic diagram of the left side structure of FIG. 1 of the present invention.
Figure 3:
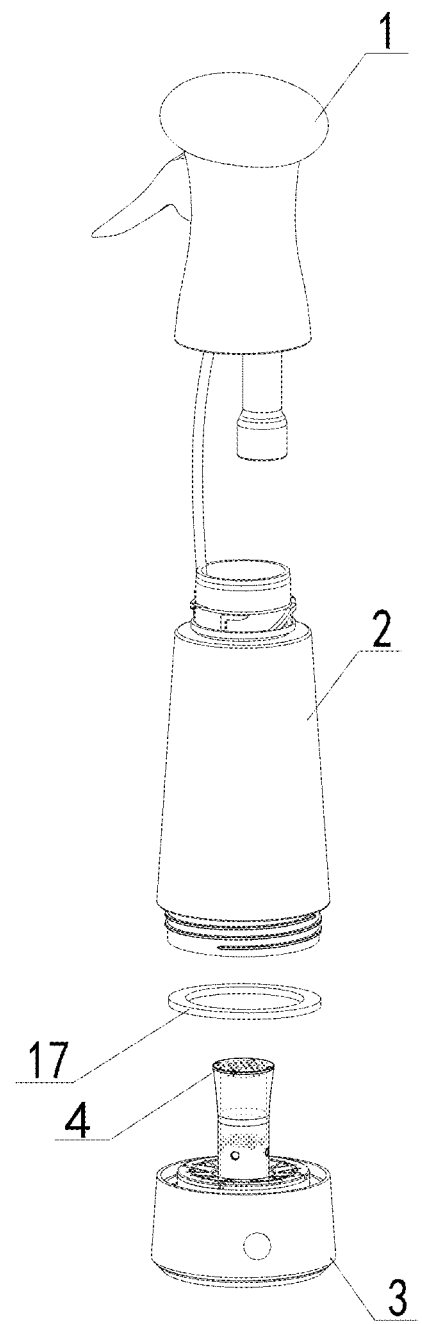
FIG. 3 is a schematic diagram of the explosive structure of FIG. 1 of the present invention.
Figure 4:
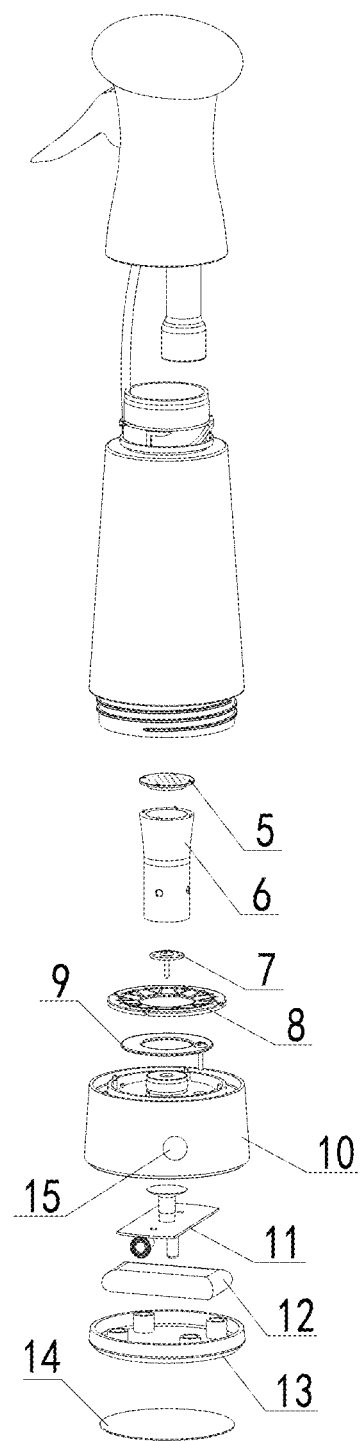
FIG. 4 is a schematic diagram of the explosive structure of FIG. 3 of the present invention.

Please refer to FIG. 1-4 for split type sterilization electrolytic silver ion spray device, which comprises a sprinkler head 1, a bottle body 2 and an electrolytic device 3. The electrolytic device 3 comprises an anode 7, a decorative cover 8, a cathode 9, an electrolytic device shell 10, a circuit board 11, a lithium battery 12 and an electrolytic device base 13. The bottom of the electrolytic device shell 10 is clamped with an electrolytic device base 13. The base of the electrolytic device 13, as a part of the electrolytic device 3, plays the role of protecting the internal circuit board 11. The base of the electrolytic device 13 and the electrolytic device shell 10 are connected and locked with four screws to play the role of sealing and waterproof. The electrolytic device shell 10, as a part of the electrolytic device 3, plays the role of protecting the internal circuit board 11 and decoration. At the same time, the internal thread is installed and connected with the thread of the bottle body 2, and the seal ring 17 is set to play the role of waterproof and moisture proof. At the same time, the connection of the thread plays a detachable and separable role. The purpose of disassembly is to replace anode 7 with a new one when anode 7 is severely damaged. The top of the electrolysis device base 13 is equipped with a lithium battery 12, which provides the required electrical energy for the electrolytic device 3. During the electrolysis process, the current passes through the electrolyte solution and causes an oxidation-reduction reaction on anode 7 and cathode 9, releasing silver ions, and these currents are provided by the battery. The lithium battery 12 is electrically connected to the circuit board 11, which can control the opening and closing of the equipment by means of a switch circuit and achieve automatic opening and closing of the equipment. The circuit board 11 is electrically connected with cathode 9 and anode 7, and the cathode 9 and anode 7 make the flow of electrons generated on the positive electrode flow from the positive electrode to the negative electrode through the internal circuit, thereby achieving the energy conversion. The cooperative work of positive and negative electrodes enables the electrolysis process to proceed smoothly, achieving effective utilization and conversion of energy. Cathode 9 is made of stainless steel, and anode 7 is made of elemental silver. An oxidation reaction is found on the surface of anode 7 when conducting electricity, through which silver ions are released into the water. A decorative cover 8 is installed on the top of cathode 9, which is installed above cathode 9 to serve as a decoration. Among them, the interior of the electrolytic device shell 10 is provided with a screw groove, and the internal screw of the screw groove is connected with the bottle body 2. The surface of the bottle body 2 is adhered to a seal ring 17, and the outer arc surface of the seal ring 17 is adhered to the electrolytic device shell 10.

Among them, there is a resin tank 4 inside the electrolysis device 3, which is used to store silver ion exchange resin for capturing and adsorbing silver ions decomposed by anode 7. The resin tank 4 includes a resin tank cover 5 and a resin tank body 6. The resin tank cover 5 is used to lock the silver ion exchange resin and restrict its movement within the resin tank body 6. The resin tank body 6 is used to store silver ion exchange resin. The surface of anode 7 is equipped with a resin tank body 6, and the top of the resin tank body 6 is equipped with a resin tank cover 5.

Among them, the bottom of electrolysis device 3 is equipped with non-slip mat 14, whose main function is to prevent the bottle body from sliding and keep it in a stable state. The top of bottle body 2 is equipped with a sprinkler head 1, which can introduce the disinfectant containing silver ions into the atomizing nozzle 1 through a pipe to achieve the effect of spray. The bottle body 2 is used as the storage container for the disinfectant containing silver ions after electrolysis. The function of electrolysis device 3 is to generate electrolytic reaction, decompose silver ions, and play the role of disinfection and sterilization.

Among them, the left side of the outer arc surface of the bottle body 2 is equipped with a charging port 16, which is used as an interface to connect the power supply for charging, and its main function is to provide power supply for the equipment to ensure that the equipment can work normally and maintain sufficient battery power. The right side of the outer arc surface of the bottle body 2 is equipped with an electrolytic switch 15, whose main function is to control the on/off of the current in the circuit. When the switch is opened, the current in the circuit can flow; When the switch is closed, the current in the circuit is cut off. By opening or closing the switch, the working status of the circuit can be easily controlled, thereby achieving specific circuit functions.

Working principle: In the process of operation, the operator fills tap water into the bottle body 2 in advance, and then obtains silver ions through the electrolytic device 3, and stores the prepared solution in the bottle body 2. Then, the silver ion solution is applied to the object to be purified through the sprinkler head 1. Because the anode 7 in the electrolytic device 3 is made of silver metal element, the lithium battery 12 is controlled by electrolytic switch 15 to achieve discharge and form a loop. At this time, the surface of the anode 7 soaked in water undergoes an oxidation reaction, and silver atoms lose electrons and become silver ions and are released into solution. In this process, when there are enough silver ions in water, they will obtain electrons on cathode 9 and be reduced to silver atoms, which will deposit on cathode 9. In order to prevent the silver ions in the water body from being reduced to the maximum extent, we have added a resin tank 4 inside. The resin tank 4 is equipped with silver ion exchange resin which can effectively capture and adsorb free silver ions. The circuit board 11 can automatically control the electrolysis time. After the electrolysis is completed, the power is automatically cut off. Part of the adsorbed silver ions during electrolysis can be washed with hot water to increase the porosity of resin, so as to release silver ions, assisting in increasing the silver ion content in the preparation solution.

It should be noted that in this article, relational terms such as first and second are only used to distinguish one entity or operation from another entity or operation, and do not necessarily require or imply any such actual relationship or order between these entities or operations. Furthermore, the terms "includes", "contains" or any other variation thereof are intended to encompass non-exclusive inclusion, such that a process, method, item or device that includes a series of elements not only includes those elements but also includes other elements not expressly listed, or also includes elements inherent to such process, method, item, or device.

Although embodiments of the present invention have been demonstrated and described, those of ordinary skill in the art can understand that these embodiments can be changed, modified, replaced, and modified in various ways without deviating from the principles and spirit of the present invention, and that the scope of the present invention is limited by the attached claims and their equivalents.

The invention claimed is:

1. A split type sterilization electrolytic silver ion spray device comprising a sprinkler head (1), a bottle body (2) and an electrolytic device (3), the electrolytic device (3) comprising an anode (7), a decorative cover (8), a cathode (9), an electrolytic device shell (10), a circuit board (11), a battery (12) and an electrolytic device base (13), wherein a bottom of the electrolytic device shell (10) is clamped with the electrolytic device base (13), a top of the electrolytic device base (13) is equipped with the battery (12), the battery (12) is electrically connected with a circuit board (11), the battery (12) and the circuit board (11) are located between the electrolytic device shell (10) and the electrolytic device base (13), the circuit board (11) is electrically connected with the cathode (9) and the anode (7), and a top of the cathode (9) is equipped with the decorative cover (8), wherein the bottle body (2) is detachably connected the electrolytic device shell (10), the bottle body (2) and the electrolytic device shell (10) form a space for accommodating electrolyte solution, the anode (7) and the cathode (9) are located in the space and configured to contact and electrolyze the electrolyte solution, a material of the anode (7) is silver, such that silver ions are generated during electrolytic process, the sprinkler head (1) is connected to an end of the bottle body (2) far away from the electrolytic device shell (10) and configured to spray the electrolyte solution with the silver ions for sterilization.

2. The split type sterilization electrolytic silver ion spray device according to claim 1, wherein the electrolytic device shell (10) is equipped with a screw groove, and an internal thread of the screw groove is connected with an outernal thread of the bottle body (2), a bottom surface of the bottle body (2) is fitted with a seal ring (17), and an outer arc surface of the seal ring (17) is fitted with the electrolytic device shell (10), the seal ring (17) is configured to avoid an electrolyte solution leakage at a connection position between the electrolytic device shell (10) and the bottle body (2).

3. The split type sterilization electrolytic silver ion spray device according to claim 1, wherein the electrolytic device (3) further comprises a resin tank (4), the resin tank (4) comprises a resin tank cover (5) and a resin tank body (6), a top of the resin tank body (6) is equipped with the resin tank cover (5), a bottom of the resin tank body (6) is connected to the decorative cover (8), the resin tank (4) is configured to accommodate the anode (7) and resin, and the resin is configured to capture and adsorb the silver ions.

4. The split type sterilization electrolytic silver ion spray device according to claim 1, wherein a bottom of the electrolytic device base (13) is equipped with an non-slip mat (14).

5. The split type sterilization electrolytic silver ion spray device according to claim 1, wherein a first side of the bottle body (2) is equipped with a charging port (16), and a second side opposite to the first side of the bottle body (2) is equipped with an electrolytic switch (15), when the electrolytic switch (15) is opened, a current flows the anode (7), the electrolyte solution and the cathode (9), and the anode (7) releases the silver ions.

6. The split type sterilization electrolytic silver ion spray device according to claim 1, wherein the cathode (9) is made of stainless steel material.

7. The split type sterilization electrolytic silver ion spray device according to claim 1, wherein the electrolyte solution is tap water.

8. A split type sterilization electrolytic silver ion spray device comprising a sprinkler head (1),
a bottle body (2) connected to the sprinkler head (1), and
an electrolytic device (3) connected to the bottle body (2), the electrolytic device (3) comprising an anode (7), a cathode (9), an electrolytic device shell (10), a circuit board (11), and a battery (12), wherein the battery (12) and the circuit board (11) are located in the electrolytic device shell (10), the battery (12) and the circuit board (11) are electrically connected with the cathode (9) and the anode (7), the bottle body (2) and the electrolytic device shell (10) form a space for accommodating electrolyte solution, the anode (7) and the cathode (9) are located in the space and configured to contact and electrolyze the electrolyte solution, wherein a material of the anode (7) is silver, when a current flows the anode (7), the electrolyte solution and the cathode (9), silver ions are generated by the anode (7) and are released into the electrolyte solution, such that the sprinkler head (1) is able to spray the electrolyte solution with the silver ions for sterilization.

9. The split type sterilization electrolytic silver ion spray device according to claim 8, the electrolytic device (3) is detachably connected to the bottle body (2), a seal ring (17) is disposed between a connection position between the electrolytic device shell (10) and the bottle body (2) to avoid an electrolyte solution leakage.

10. The split type sterilization electrolytic silver ion spray device according to claim 9, wherein the electrolytic device shell (10) is equipped with a screw groove, an internal thread of the screw groove is connected with an outernal thread of the bottle body (2).

11. The split type sterilization electrolytic silver ion spray device according to claim 8, wherein the electrolytic device (3) further comprises a resin tank (4) disposed in the space, the resin tank (4) comprises a resin tank cover (5) and a resin tank body (6), a top of the resin tank body (6) is connected with the resin tank cover (5), the resin tank (4) is configured to accommodate the anode (7) and resin, and the resin is configured to capture and adsorb the silver ions.

12. The split type sterilization electrolytic silver ion spray device according to claim 11, wherein the electrolytic device shell (10) comprises a top surface for supporting the cathode (9) and the anode (7) and a decorative cover (8) disposed on the cathode (9), the cathode (9) and the decorative cover (8) are ring shaped and disposed around the anode (7), and the resin tank (4) is connected to the decorative cover (8) and accommodates the anode (7).

13. The split type sterilization electrolytic silver ion spray device according to claim 12, wherein the resin tank (4) is detachably connected to the decorative cover (8) so as to expose the anode (7) and replace a new anode (7).

14. The split type sterilization electrolytic silver ion spray device according to claim 8, wherein the electrolytic device (3) further comprises an electrolytic device base (13) connected to a bottom of the electrolytic device shell (10), the battery (12) and the circuit board (11) are disposed on the electrolytic device base (13).

15. The split type sterilization electrolytic silver ion spray device according to claim 14, wherein the electrolytic device (3) further comprises a non-slip mat (14) disposed at a bottom far away from the electrolytic device shell (10).

16. The split type sterilization electrolytic silver ion spray device according to claim 8, wherein the electrolytic device (3) further comprises an electrolytic switch (15) disposed at the electrolytic device shell (10), when the electrolytic switch (15) is opened, a current flows the anode (7), the electrolyte solution and the cathode (9), and the anode (7) releases the silver ions.

17. The split type sterilization electrolytic silver ion spray device according to claim 16, wherein the electrolytic device (3) further comprises a charging port (16) disposed at the electrolytic device shell (10), and the electrolytic switch (15) and the charging port (16) are located at two opposite sides of the electrolytic device shell (10).

18. The split type sterilization electrolytic silver ion spray device according to claim 8, wherein the electrolyte solution is tap water.

19. The split type sterilization electrolytic silver ion spray device according to claim 8, wherein the cathode (9) is made of stainless steel material.

20. A split type sterilization electrolytic silver ion spray device comprising
a sprinkler head (1),
a bottle body (2) connected to the sprinkler head (1), the bottle body (2) configured for accommodating electrolyte solution, and
an electrolytic device (3) comprising an anode (7), a cathode (9), a circuit board (11), and a battery (12), the battery (12) and the circuit board (11) electrically connected with the cathode (9) and the anode (7), the anode (7) and the cathode (9) configured to contact and electrolyze the electrolyte solution,
wherein a material of the anode (7) is silver, when a current flows the anode (7), the electrolyte solution and the cathode (9), silver ions are generated by the anode (7) and are released into the electrolyte solution, such that the sprinkler head (1) is able to spray the electrolyte solution with the silver ions for sterilization.

* * * * *